United States Patent [19]

Tenczar

[11] 4,149,534

[45] Apr. 17, 1979

[54] STERILE FILM CONNECTORS

[76] Inventor: Francis J. Tenczar, 5335 W. Touhy, Skokie, Ill. 60077

[21] Appl. No.: 794,605

[22] Filed: May 6, 1977

[51] Int. Cl.² ............................................. A61M 5/00
[52] U.S. Cl. ............................. 128/214 R; 128/214.2; 285/150; 285/423
[58] Field of Search ............... 285/150, DIG. 16, 423; 128/214 R, 214 D, 214.2; 138/89

[56] References Cited

U.S. PATENT DOCUMENTS

| | | | |
|---|---|---|---|
| 3,177,870 | 4/1965 | Salem et al. | 128/214.2 |
| 3,306,563 | 2/1967 | Soto | 128/214 R X |
| 3,613,663 | 10/1971 | Johnson | 128/214 R X |
| 3,865,411 | 2/1975 | Rowe et al. | 285/363 |
| 4,007,738 | 2/1977 | Yoshino | 128/214 D |
| 4,019,512 | 4/1977 | Tenczar | 128/214.2 X |
| 4,022,205 | 5/1977 | Tenczar | 128/214.2 X |

Primary Examiner—Dalton L. Truluck
Attorney, Agent, or Firm—Knechtel, Valentino, Demeur & Dallas

[57] ABSTRACT

There is disclosed an improved sterile connector formed by at least two polygonal planar plastic members having the same configuration and being joined face to face in matching relationship, a common collection chamber positioned centrally between the joined members and being formed by the plastic members, a film of adhesive positioned on adjoining faces of the plastic members for holding the contacting faces together, the joined plastic members being adapted to contain at least two spaced fluid flow paths extending from outside the joined plastic members through the adhered members to communicate with the common collection chamber such that the plastic members may be adhesively joined in surrounding relation to said fluid flow paths to establish fluid communication between the flow paths through the common collection chamber in order to establish interconnection between separated fluid sources.

26 Claims, 19 Drawing Figures

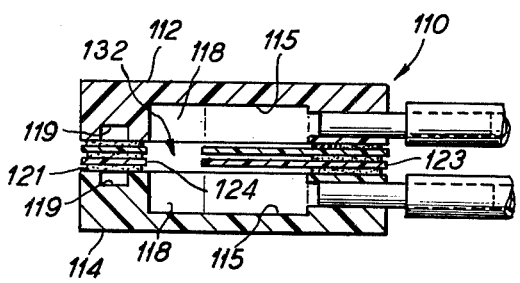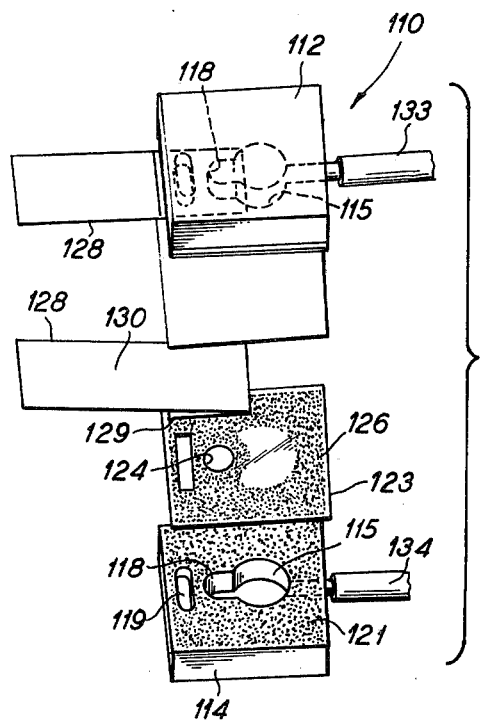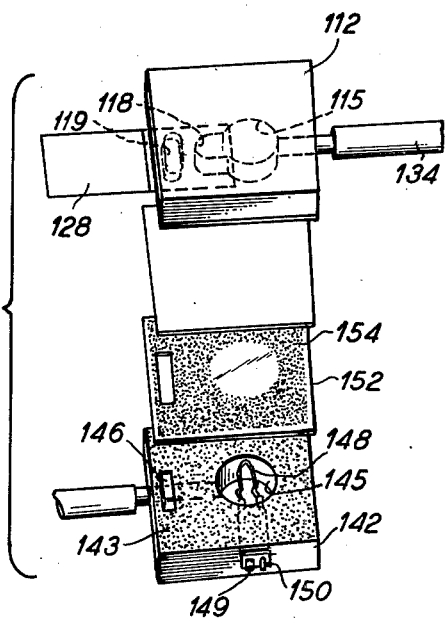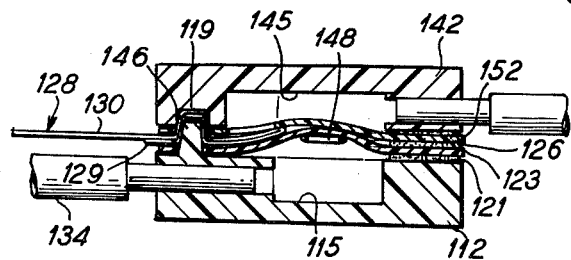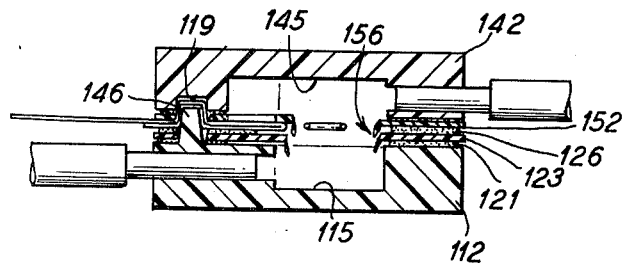

STERILE FILM CONNECTORS

BACKGROUND OF THE INVENTION

As is well known, it is often desirable within the art fields of medicine, pharmacy, chemistry and the like, to require the transfer of fluids from a separated source thereof to a delivery location. This is especially true in the medical arts where often, it is necessary or desirable to transfer fluids such as blood, parenteral solutions, and the like from a stored container to either a different container, or for direct patient usage. In most instances, the separated fluid source comprises a container and is manufactured with conduit means associated with the container and extending outwardly therefrom. In order to effect the transfer from the container to a patient or to a different container, it is necessary to have a connector which will establish a fluid flow path from the storage container to the other container or the patient. It will also be appreciated that where sterility is required, such connectors must be sterile at the inception, and must maintain a sterile environment for the fluid passing therethrough.

One of the primary difficulties in designing suitable sterile connectors is the fact that the danger of contamination from air borne materials as well as other contaminants in and around the environment surrounding the point of delivery may easily find their way into the interior portion of the present connectors. Hence, the provision of a sterile connector which may be easily manipulated by the operator to establish an assured sterile fluid flow.

It has been determined that the fabrication of a sterile connector for joining a supply source to an independent delivery location through a contaminated environment requires at least four important design steps:

1. The alignment of the connector housings;
2. Excluding of the contaminated environment;
3. Sterilization of the excluded region;
4. Penetration within the sterilized area followed by coupling of the protected internal conduits.

Due to the above noted design parameters, it has usually been necessary to design sterile connectors which are not only rigid in construction, but are rather cumbersome to use, and also require various forms of mechanical means to join the two connector bodies together in a sterile and fluid tight sealing arrangement such that a sterile environment is retained within the common collection chambers established between the two joined faces of the connector bodies.

Exemplary of the most recent developments in this particular art field is shown in U.S. Pat. No. 3,865,411 which is directed to a sterile connector for interconnecting opposed separated conduits. As exemplified by the above noted patent, the sterile connector is formed by a flanged body portion carried at the end of an appropriate conduit, and further includes a compressible gasket made from an elastomeric material. A diaphragm or pull tab cover is positioned over the adjoining face of the compressible gasket and which includes a long fold extending laterally outwardly from adjoined faces of the corresponding gasketed portions of the connector. It will further be appreciated that once the joined faces are brought together, the two gasketed portions must be clamped together by some mechanical means such as a spring-loaded clamp or snap fitting bale arrangement in order to compress the gaskets together, and maintain a seal while simultaneously removing the pull tab covers between the two faces so that a fluid flow path is established between the opposed conduits. Hence, it will be appreciated that the sterile connector actually includes two elements, including a sterile internal connector proper, and a housing serving as an environmental barrier. It will be appreciated that in such a system, contamination from the environment theoretically occurs upon removal of the housing preliminary to joining the sterile internal elements. It is for this reason that devices such as pull tab covers, which are designed to be removed upon the commencement of the joining of the two connector body members, have been designed such that once the connector housings are in proper alignment and the joining commences, the pull tab covers may be removed to establish the fluid flow path under sterile conditions.

Another system incorporated in sterile connector members has been the use of a loop of nichrome wire which is substituted for any type of mechanical penetrator. In systems of this type, the openings establishing the common chamber are usually covered with a membrane of some type and having a looped nichrome wire positioned immediately beneath one of the membranes. Once the joining faces are brought together, the loop is energized by an external voltage source, thereby to heat the wire in order to penetrate through the membranes and establish a fluid flow path. Additionally, the energizing of the nichrome wire loop functions to sterilize the immediate environment in the fluid path.

It will be appreciated from the above discussion that various difficulties have been encountered in connection with sterile connectors. For example, in many applications, such as the preparation of frozen blood, the blood is provided in flexible containers which are then placed in facilities in order to effect the freezing of the blood. In practice, such containers will assume a very thin configuration, as a package to facilitate heat transfer and freezing. The connectors must be dimensionally suited for inclusion in such a "thin" package configuration.

Even more importantly, it has been deemed desirable to provide a sterile connector concept which lends itself to thin, flexible applications, as well as to conceptionally provide a connector which is adaptable to interconnect multiple fluid sources but in a simplified manner.

OBJECTS AND ADVANTAGES

It is therefore the principal object of the invention to provide a simplified but yet highly improved sterile connector which employs an adhesive system for effecting the joining together of the connector body members, incident to establishing fluid communication between two or more separated fluid conduits.

In connection with the foregoing object, it is a further object of the invention to provide a sterile connector for connecting separated fluid sources which is formed by at least two polygonal plastic members having the same configuration and being joined face to face in matching relationship, a common collection chamber positioned substantially centrally between the joined members and formed by the plastic members, a film of adhesive positioned on adjoining faces of the plastic members for holding the contacting faces thereof together, and the joined plastic members being adapted to carry and hold at least two spaced conduits extending from outside the sterile connector through the adhered contacting faces thereof to communicate with the common collection chamber and establish a common fluid flow path.

Still in connection with the foregoing object, it is yet a further object of the invention to provide a sterile connector of the type set forth wherein the body portion of the sterile connector is formed by two polygonal plastic members, each of the members being formed by an outer thin, flexible plastic unit of sheet-like construction having an exterior surface and a contacting surface, an intermediate, thin, flexible sheet-like unit having a configuration corresponding to the outer unit, the intermediate unit having the reverse side disposed towards the contacting surface of the outer unit and an adherent side, and the intermediate unit further including a substantially central opening positioned therein, the central opening being in registry with the cenral opening of the adjacent intermediate unit of the other of the two plastic members whereby the central openings form a common collection chamber therebetween when the two members are adhered together, sealing means interposed between the contacting surface and the outer unit and the reverse side of the intermediate unit to sealingly mate the units together and each of the polygonal planar plastic members including a fluid flow path interposed between the outer unit and the intermediate unit and in fluid communication with the common collection chamber such that the sterile connector formed thereby may be easily positioned about fluid conduits emanating from separate fluid sources, with the ends of the conduit positioned adjacent to the central openings forming a common collection chamber such that a fluid flow path is established between the two separated conduits through the common collection chamber.

Still another object of the invention is to provide a sterile connector of the type set forth above, which further includes a pair of pull tab covers positioned over the corresponding central openings of the corresponding members, each pull tab cover formed from a thin elongated strip of foldable material and including a short fold overlying a portion of the film of adhesive surrounding and further overlying the central opening and with a long fold folded flat over the short fold of the pull tab cover such that each of the long folds extends laterally outwardly beyond the periphery of the plastic member, the pull tab cover and the film of adhesive characterized by a differential adhesive bonding such that a pulling force exerted on the long fold externally of the sterile connector will progressively expose the central openings thereof to form a common collection chamber.

In connection with the foregoing objects, it is yet a further object of the invention to provide a sterile connector of the type described wherein each of the polygonal planar plastic members are formed as rigid plastic members having a thickness substantially less than the length of a side thereof and wherein the common collection chamber is formed by a central opening constructed in the form of a well such that upon joining the two plastic members in face to face contact and relationship, the wells combine to form a common collection chamber.

In connection with the foregoing object, it is yet a further object to provide a sterile connector of the type described wherein the fluid flow pathways are formed as conduits extending through the body portions of each polygonal plastic member having an inner end terminating at the well, and the outer end thereof terminating in or beyond the side peripheral wall of the corresponding body portion.

Another object of the present invention is to provide a sterile connector which in one embodiment thereof, provides at least two polyhedral planar plastic members wherein one of the plastic members includes a traversing central opening traversing the member from one surface to the opposed surface, and each of the remaining plastic members includes a central opening formed as a well therein and positioned to be in registry with the traversing central opening when the plastic members are joined together, and wherein each of the plastic members includes at least one fluid flow path formed therein positioned to establish fluid communication between the corresponding central opening and the outer periphery of the member, and each of the members further including a film of adhesive positioned on one of the opposed surfaces thereof to permit at least two of the plastic members to be joined together, each of the members including a pull tab cover positioned over a portion of the adhesive film surrounding the central opening with the pull tab having a portion of the long fold thereof extending outwardly from the peripheral side of the sterile connector, whereby two or more of the plastic members may be joined together in face to face touching relationship and establish fluid communication between separated fluid sources through the common collection chamber formed by traversing the central opening and the wells in the adjoining plastic members.

In connection with the foregoing object, it is yet a further object to provide a sterile connector of the type described wherein the body portion of the sterile connector is formed by successive additions of a plurality of rigid plastic members, joined together in face to face stacked relationship, each including a traversing central opening, each traversing central opening being in registry with the next adjoining rigid plastic member central opening, and the sterile connector body being bounded by a final rigid plastic member of the type formed with a well positioned therein, one of each of the rigid plastic members with a well forming the outer ends of the stacked rigid members, and each of the plastic rigid members including conduit means formed integrally therewith and in fluid communication with the central openings of each corresponding member such that the sterile connector formed by the stack of rigid plastic members functions as a manifold to interconnect a plurality of separated fluid sources.

An additional object of the invention is to provide a further embodiment of a sterile connector wherein the sterile connector includes at least one rigid plastic member provided with a resistance heating wire loop positioned within the well thereof, and wherein each of the plastic members forming the sterile connector is further provided with a protective plastic cover overlying the film with adhesive such that upon face to face contact between the adjoining contacting faces of the sterile connector, the resistance heating wire loop may be energized by an external voltage source thereby to generate sufficient heat to fuse, penetrate, seal and sterilize the plastic protective covers and to establish the common collection chamber.

Still further in connection with the above noted objects, it is a further object to provide a sterile connector of the type described including a nichrome heating wire loop wherein the rigid plastic member having the well formed therein further includes a bud well adjoining and in open communication with the main well and further having a straight groove extending across the contacting face thereof and reaching to adjoining sides thereof, and the opposed one of the rigid plastic members includes a straight tongue positioned to seat within the groove of the opposed rigid plastic member when the contacting faces are joined together, such that the pair of pull tabs provided over the adhesive film and the corresponding wells are adapted to be seated and locked by the tongue and groove arangement thereby to prevent the unauthorized removal of the pull tabs such that the common collection chamber is established by energizing the nichrome heating wire loop to penetrate the membranes interposed therebetween.

An additional object of the invention is to provide a sterile connector of the type described above wherein the two rigid plastic members forming the sterile connector each include a main well and a bud well, but wherein both of the contacting surfaces are provided with the groove arrangement such that upon joining the two rigid plastic members together in face to face relationship, the common collection chamber may be established by the removal of the pull tab as the plastic members are adhesively joined together, such that rigid plastic members of the type described may be used either with or without the nichrome heating wire loop arrangement.

Further features of the invention pertain to the particular arrangement of the elements and parts whereby the above-outlined and other operating features thereof are attained.

The invention both as to its organization and methods of operation will best be understood by reference to the following specification taken in conjunction with the accompanying drawings which are described hereinbelow.

BRIEF SUMMARY OF THE INVENTION

Briefly stated, the present invention provides an improved sterile connector which is formed of at least two plastic members which are adjoined together adhesively, and which provide a common collection chamber traversing the contacting surface of the two members. In addition, a fluid flow path is provided between the common collection chamber and the outer periphery of the sterile connector so that the connector may be used to interconnect separated fluid sources.

One embodiment of the invention provides a sterile connector of the type described which is formed of flexible sheetlike plastic material such that a simplified version of a sterile connector which minimizes storage space and which may be manipulated quite easily, is provided. In another embodiment herein, the sterile connector is formed of two rigid plastic members which, again, are adhesively joined together to form a common collection chamber and having fluid flow paths in the form of channels or conduits molded integrally therewith.

In still another embodiment of the invention disclosed herein, a sterile connector formed of a plurality of rigid plastic members is provided wherein the rigid plastic members which are utilized as intermediate members are each provided with a traversing central opening such that a plurality of the members may be stacked together and adhesively joined, the stacked grouping bounded by end rigid members, and wherein each of the rigid members includes at least one conduit in fluid communication with the corresponding central opening, such that a manifold effect is achieved. In this manner, a plurality of separated fluid sources may be sequentially interconnected as desired by the operator.

BRIEF DESCRIPTION OF THE DRAWINGS

FIG. 15 is a side elevational view, in cross section, showing still another embodiment of the sterile connector of the present invention wherein each central opening formed by a well further includes a bud well for joining to and in communication therewith with the pull tab covers removed;

FIG. 16 is a perspective exploded view showing the component parts of a sterile connector as exemplified in FIG. 15, and two like rigid plastic members with pull tabs;

FIG. 17 is a side elevational view, in cross section, showing an additional embodiment of the invention where the two rigid members include a tongue and groove arrangement to entrap the pull tab cover therein and further including a nichrome heating wire loop arrangement;

FIG. 18 is an exploded view, in perspective, showing the component elements of the embodiment of the invention as depicted in FIG. 17 of the drawings; and FIG. 19 is a side elevational view, in cross section, of the embodiment as depicted in FIG. 17, illustrating the configuration of the common collection chamber once the nichrome heating wire loop has been energized.

DETAILED DESCRIPTION OF THE DRAWINGS

Figure 1:
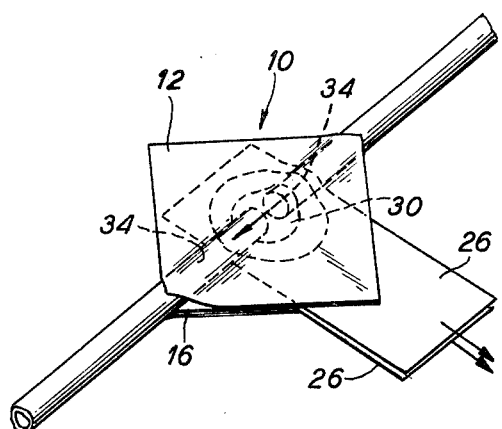
FIG. 1 is a perspective view of one embodiment of a sterile connector of the present invention wherein the sterile connector is formed of a flexible, thin sheet-like material and including a pull tab system and formed fluid flow path for introducing conduits therein.

With reference to the drawings, the simplified embodiment of the invention is depicted in FIGS. 1 through 5 thereof. As shown therein, there is illustrated a sterile connector 10 which is formed by a plastic outer unit 12 which is comprised of a thin, flexible, sheet-like plastic material. The outer unit 12 is shown to include an exterior surface 13 and a contacting surface 14, and in this embodiment, is shown to be generally rectangular in configuration. Immediately below the outer unit 12 is provided an intermediate unit 16, which is formed of a like material, that being a thin, flexible sheet-like plastic material, and further including a reverse surface 17 which is positioned toward the contacting surface 14 of the corresponding outer unit, and an adherent surface 18. It will be observed that the reverse surface 17 of the intermediate unit 16 is provided with a film of adhesive generally referred to by the numeral 20, such that the contacting surface 14 of the outer unit 12 and the reverse surface 17 of the intermediate unit 16 may be adhered together.

Alternatively, the units may be joined together by a heat sealing process as opposed to using an adhesive. The intermediate unit 16 is further provided with a central opening 22 such that the central openings 22 in the joining intermediate unit 16 are in registry one with the other. It will be further noted that the film of adhesive 20 on the reverse surface 17 of the intermediate 16 terminates at a point spaced slightly from the periphery of the central opening 22. In addition, it will be observed that the adherent surface 18 of the intermediate unit 16 is similarly provided with a second adhesive film 24, which in this embodiment is shown to cover the area around the central opening 22.

The sterile connector 10 is substantially completed by the provision of a pair of pull tab covers 26 which are designed and constructed to overlie the adherent surface 18 of the intermediate unit 16.

Each of the pull tab covers 26 is formed of a plastic material which has a unique relationship with the adhesive film 24 such that a bonding differential is created in order to permit ease of removal of the pull tab covers 26 as will be more fully described hereinbelow.

The pull tab covers 26 are shown to include a short fold 27 which overlies the adhesive film 24 as well as the corresponding central opening 22 formed in the intermediate unit 16. There is also provided a long fold 29 of the pull tab cover 26 which folds back over the short fold 27 and extends laterally outwardly beyond the peripheral border of the sterile connector 10.

As depicted in FIG. 1, the pull tab covers 26 may be removed by simply grasping the sterile connector in one hand, and grasping the external portions of the pull tab covers 26 in the opposed hand, applying manual pressure. It will be apparent that as the long folds 29 of the pull tab covers 26 are pulled away from the body of the sterile connector 10, the corresponding short folds 27 will progressively expose the central openings 22 above the intermediate units 16 which are now in registry. The underlying sterile adhesive layers are simultaneously uncovered and fused to exclude the environment.

The sterile connector 10 functions by providing a common collection chamber generally represented by the numeral 30 formed by the corresponding central openings 22 in the two intermediate units 16 when mating connectors are joined. As shown in both FIGS. 1 and 2 of the drawings, a pair of conduit 32 may be provided, each of which has an inner end which, in use will reside within the common collection chamber 30, and an external end which terminates in fluid communication with a separate fluid source. In this manner, the fluid source represented by each of the two conduits 32 may be interconnected through the common collection chamber 30 of the sterile connector 10. As further shown in FIGS. 1 and 2, the conduits 32 are retained in position by means of the film of adhesive 20 which is interposed between the reverse surface of the intermediate unit 16 and the contacting surface 14 of the outer unit 12. Alternatively, and as depicted specifically in FIG. 1, the sterile connector 10 may be formed with a fluid flow path 34 which is defined by opposed areas between the outer unit 12 and the intermediate unit 16 wherein portions of the film of adhesive 20 are omitted such that the two sheets of material are unadhered along the fluid flow pathway 34. Hence, in this embodiment, where the separated fluid sources have conduit extending outwardly therefrom, the ends of the conduit 32 may simply be inserted through the fluid flow path 34 established in the sterile connector body 10 as the pull tab covers 26 are removed in order to expose the common collection chamber 30. Where heat sealing is employed as an alternative to the use of an adhesive system, the fluid flow path 34 is formed by omitting heat sealing along the path of the fluid flow path 34.

Figure 2:
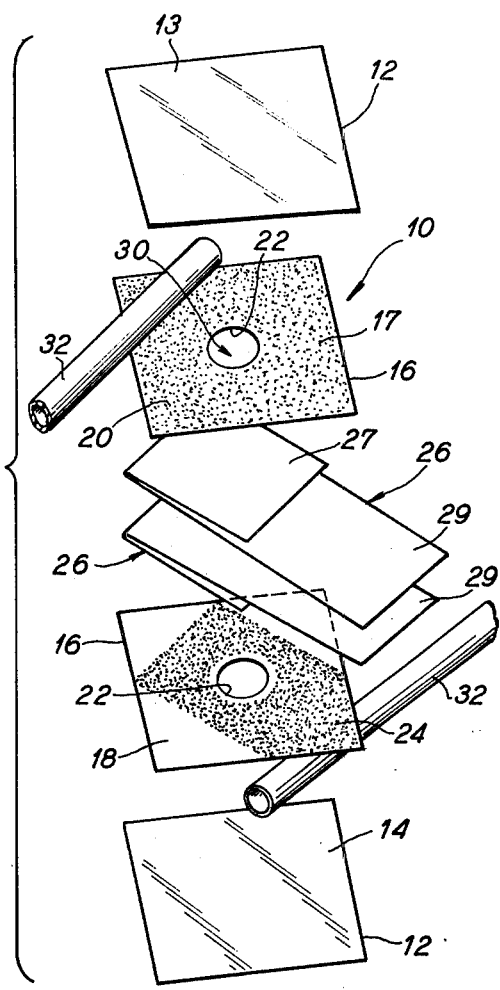
FIG. 2 is an exploded view of the sterile connector as shown in FIG. 1 illustrating the various component portions thereof.

It will therefore be appreciated that a sterile connector of the type depicted in FIGS. 1 and 2 may be provided either with one or two conduits extending outwardly therefrom and suitable for attachment to a separated fluid source, or, the sterile connector 10 may simply function to accommodate the insertion therein of separated conduit 32 which emanate from separate fluid sources, which is accomplished prior to the mating of the connector bodies.

Figure 3:
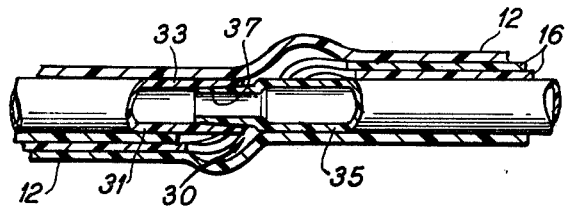
FIG. 3 is a side elevational view, in cross section, of another form of the sterile connector as shown in FIGS. 1 and 2 wherein the conduits are provided with male and female coupling elements.
Figure 4:
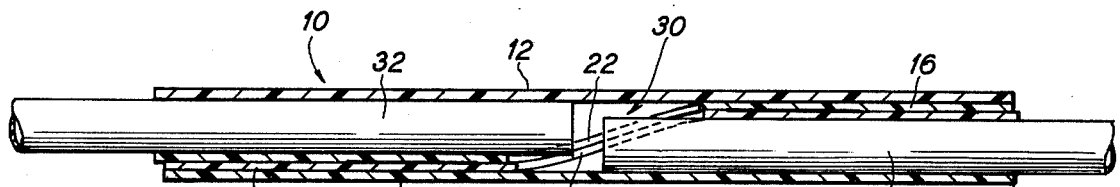
FIG. 4 is a side elevational view, in cross section, of a sterile connector with the conduits in position with the pull tab system.

The embodiment of the sterile connector 10 illustrated in FIG. 3 of the drawings is essentially as described above in connection with FIGS. 1 and 2 of the drawings, the only variation being in the conduit provided. It will be observed that the first conduit 31 is provided with a female coupling end 33 while the opposed conduit 35 is provided with a male coupling end 37. It will be appreciated that as the conduits 31 and 35 are inserted into the sterile connector 10, and the pull tab covers 26 removed the corresponding male coupling end 37 and female coupling end 33 may be connected by grasping the external portions of the sterile connector 10 and simply forcing the male coupling end 37 into the female coupling end 33. Due to the thin and flexible nature of the plastic sheet-like material of which the sterile connector 10 is formulated, the sterile connector 10 has sufficient play and give in order to permit the coupling action to occur. As shown in FIG. 3, the area around the common collection chamber 30 will be slightly bulged, but in all respects, an essentially sterile and open flow path will be established.

Figure 6:
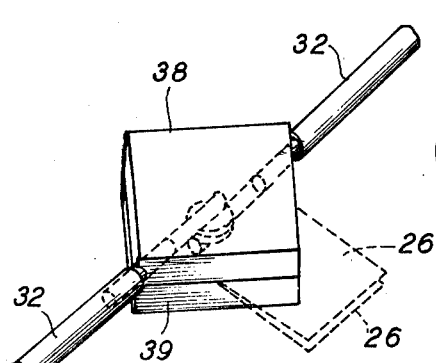
FIG. 6 is a perspective view illustrating the pressure blocks which may be provided with a sterile connector of the present invention for pressingly mating the contacting the face of the flexible plastic members forming the sterile connector body.

In FIG. 6 of the drawings, there is illustrated a pair of pressure blocks 38 and 39 which may be employed for the purpose of overlying the elements of the sterile connector 10 once the conduits 32 have been appropriately positioned in place. The pressure blocks 38 and 39 function to maintain registry of the flat flexible film connectors and facilitate joining of the adhesive layers progressively exposed as the tab covers 26 are removed. In the embodiment shown in FIG. 6, the pressure blocks 38 and 39 are formed of a solid material, such as wood blocks, however, it will be appreciated that the contacting surfaces may be of compressible material (i.e. rubber) to assure even application of pressure in order to effect a good seal between the components of the sterile connector 10. It will be further observed that the pressure blocks 38 and 39 may appropriately be channeled in order to accommodate the positioning of the conduits 32, should these be of rigid material.

Figure 5:
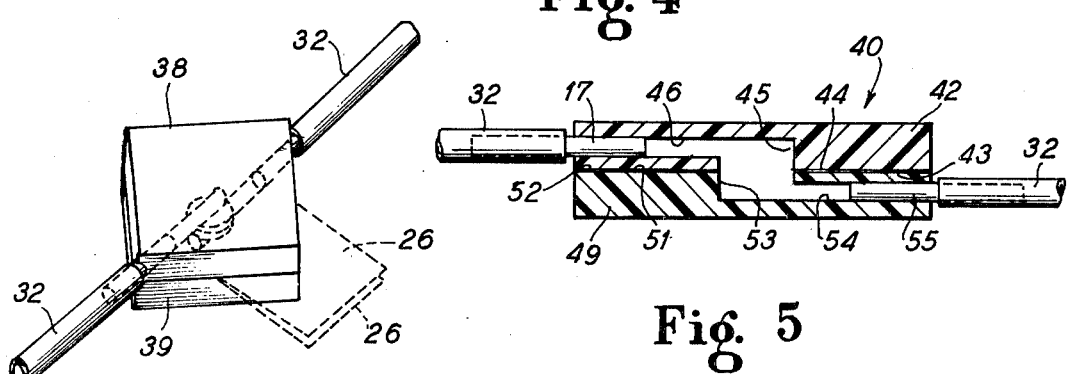
FIG. 5 is a side elevational view, in cross section, of another embodiment of a sterile connector wherein the connector body members are each formed of rigid plastic wafer having a thickness less than the length of a side and wherein the fluid flow paths are formed as conduits molded within the plastic wafer member.

Another embodiment of the invention is depicted in FIG. 5 of the drawings. There is shown a sterile connector 40 formed of two rigid plastic members 42 and 49 respectively. The plastic member 42 is shown to include a contacting surface 43 which carries a film of adhesive 44 positioned thereon. In addition, positioned centrally in the plastic member 42 is a central opening 45 which is formed as a well extending inwardly from the contacting surface 43 thereof. In open and fluid communication with the well 45 is channel conduit 46 which extends from the outer periphery of the sterile connector 40 to the central opening well 45. It will be observed that both the well 45 as well as the channel conduit 46 are molded as part of the rigid plastic member 42 during the manufacturing process. If desired, a mounting tube fitting 47 may be incorporated in the channel conduit 46 in order to accommodate the insertion thereon of a conduit 32 which emanates from a separate fluid source.

The opposed rigid plastic member 49 is constructed similar to the rigid plastic member 42 and includes a contacting surface 51 which carries a film of adhesive 52. Similarly, there is formed a central opening well 53 which is in open and fluid communication with channel conduit 54. A mount tube fitting 55 is provided in the channel conduit 54 to accommodate the mounting of an appropriate conduit 32 thereon.

Figure 8:
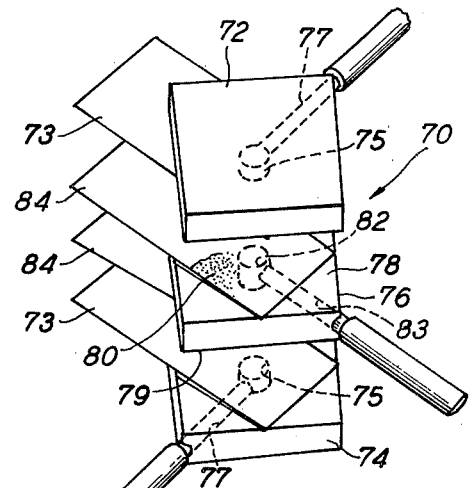
FIG. 8 is an exploded view of still another embodiment of the sterile connector of the present invention wherein the sterile connector is formed of three separate polyhedral planar plastic members wherein the intermediate member is provided with a traversing central opening and the common collection chamber is formed by having the wells and the two outer members in registry with the traversing central opening in the intermediate member permitting the connection of three separated fluid sources.

While not shown in FIG. 5 of the drawings, as illustrated in FIGS. 1, 2 and 8 of the drawings, a pull tab system similar to the one described in connection with the embodiment of FIGS. 1 and 2 as well as 8 is provided for the sterile connector 40 as depicted in FIG. 5. Hence, in order to join the two rigid plastic members 42 and 49 together, the corresponding films of adhesive 44 and 52 are exposed and brought into touching face to face contact. Once the corresponding central opening wells 45 and 53 have been aligned in registry with one another, the pull tabs are removed and the pressure applied to the external surfaces of the corresponding members 42 and 49 in order to securely adhere the adhesive films together. In practice, the pull tab covers of the embodiments disclosed herein are not removed until the corresponding adhesive films have made contact and some slight pressure has been applied. In this manner, the sterility of the common collection chamber formed between the respective members will be insured in that the outer environmental factors will be excluded therefrom. It will also be apparent that in usual application, the connector is joined to a conduit integrally with a sterilized fluid source or container. After joining of the mating connectors, removal of the tab system is accomplished under a condition of total environmental exclusion so as to protect the pre-existing sterility of the common collection chamber when establishing a fluid path between the separated fluid sources.

Figure 7:
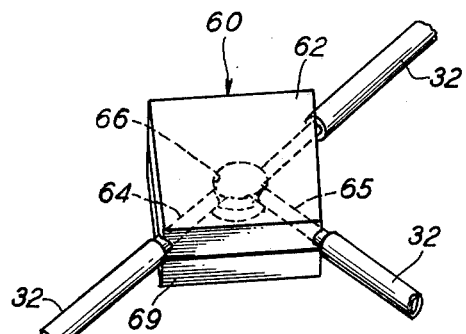
FIG. 7 is a perspective view showing still another embodiment of the sterile connector of the present invention formed by polyhedral rigid plastic members wherein one of the plastic members includes a pair of conduits extending outwardly from and in fluid connection with the common collection chamber in order to permit the inner connection of three separated fluid sources.

With reference to FIG. 7 of the drawings, still another embodiment of the subject sterile connector of the present invention is illustrated. In this embodiment, there is shown a sterile connector 60 which is formed from a first rigid plastic member 62 and a second rigid plastic member 69. In all respects, the corresponding rigid plastic members 62 and 69 are formed in the same manner as the embodiment depicted in FIG. 5 of the drawing, with the exception that the first rigid plastic member 62 is shown to include two channel conduits 64 and 65 respectively. It will be observed that the two channel conduits 64 and 65 emanate from the central opening well 66 at the inner ends thereof and terminate at the outer pheriphery of the sterile connector at the outer ends thereof. Once again, the channel conduits 64 and 65 may be provided with mount tube fittings in order to carry appropriate conduits 32 thereon. By providing a sterile connector 60 which is formed of two rigid plastic members 62 and 69 which assume a quadrilateral configuration, a number of sides and surfaces are available for providing a channel conduit. As shown in FIG. 7, the two channel conduits 64 and 65 assume a Y-shaped configuration with the outer ends terminating into the opposed corners of the corresponding rigid plastic member 62. It will be appreciated, however, that additional sides and surfaces of the member 62 are available for additional channel conduits to be molded into the member 62. Hence, the purpose of illustrating the embodiment of FIG. 7 is to indicate that more than one channel conduit may be provided in each of the rigid plastic members 62 and 69 as well. It is therefore possible to design a sterile connector 60 of this type wherein a plurality of separated fluid sources may be interconnected through a common collection chamber.

Once again, as previously indicated, the structure of each of the rigid plastic members 62 and 69 is identical to what has been described in connection with the embodiment of FIG. 5, including the adhesive system as well as the pull tab system.

In FIG. 8 of the drawings, still another version and embodiment of a sterile connector system is illustrated. As shown therein, there is illustrated a sterile connector 70 which is formed by a plurality of members as described hereinbelow. It will be observed that in this instance, there is shown a series of three plastic rigid members including outer rigid members 72 and 74, and an intermediate rigid plastic member 76. The two outer rigid plastic members 72 and 74 are constructed in the same manner and are identical to the members shown in FIG. 5 of the drawings. Hence, there is provided an adhesive system and a pull tab system of the same type described with regard to FIGS. 1 and 2 of the drawings. The pull tabs are generally represented by the numeral 73 throughout. In addition, each of the members 73 and 74 are provided with central opening wells 75 and channel conduits 77.

The intermediate plastic member 76 permits a wider latitude of use for the sterile connector 70 by permitting, once again, the interconnection of a multiple number of separated fluid sources. The intermediate plastic member 76 is constructed to include opposed contacting surfaces 78 and 79, each of which is provided with a film of adhesive 80 in the manner described hereinabove. There is further provided a central opening 82 which traverses the member 76 between the opposed contacting surfaces 78 and 79. Hence, as opposed to being formed as a well set into one of the contacting surfaces, the traversing central opening 82 permits fluid flow through the entire member 76. It will also be observed that there is provided a channel conduit 83 which, at its inner end, is in fluid and open communication with the traversing central opening 82, and terminates at its outer end at the outer periphery of intermediate plastic member 76.

It will further be appreciated that when the intermediate plastic member is interposed between the two opposed outer members 72 and 74, and the contacting surfaces thereof are adhered together by removal of all of the pull tabs including the pull tab covers 84 associated with the opposed contacting surfaces 78 and 79 in the intermediate member 76, a stacking arrangement of the members is achieved in the nature of a manifold such that a plurality of separated fluid sources may now be interconnected. It will also be appreciated that one can incorporate as many intermediate plastic members 76 as desired since each of the members would have a traversing central opening 82 and its own channel conduit 83 in open and fluid communication therewith. Hence, any number of the intermediate plastic members 76 may be interposed between the outer opposed plastic members 72 and 74 to permit the interconnection of any number of separate fluid sources.

In addition, it would be appreciated that the operator may commence the construction of a manifold system type sterile connector 70 and can add to the stack at any time. In this instance, the operator would commence with one of the outer members 72 to which would be adhered any number, as desired, of intermediate members 76. The exposed outer side of the last intermediate member 76 placed in stacking relationship could be covered with any type of a protective cover or film until ready for subsequent use. In this manner, the operator could commence the construction of a manifold system over a period of days, or even weeks, and continue to add to the stack until some ultimate point is reached at which point, the operator would simply complete the manifold system by providing the final opposed outer member 74 adhered to the last stacked intermediate member 76.

It is also contemplated that where a manifold type system is employed to interconnect a multiple of fluid sources, the various opposed outer plastic members 72 and 74 as well as a number of the intermediate plastic members 76 may be color coded to indicate particular fluids which should be connected to the rigid plastic members respectively. In view of the fact that it it is contemplated that the rigid plastic members will be formed of a plastic material and molded to the desired configuration, color coding is certainly not only feasible but contemplated within the scope of the present invention.

Figure 9:
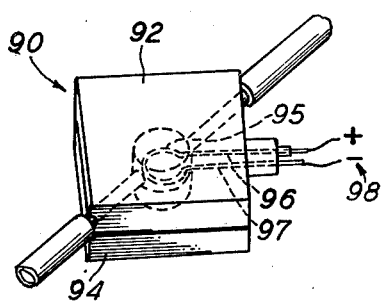
FIG. 9 is a perspective view, partly in cross section, showing still another embodiment of the present invention wherein the sterile connector is provided with a resistance heating wire loop in order to establish the common collection chamber.

As shown in FIG. 9 of the drawings, the sterile connectors of the present invention similarly permit the adaptability of the sterile connectors to the inclusion of the nichrome heating wire concept. Hence, with reference to FIG. 9, there is shown an alternate embodiment of a sterile connector 90 which, again, is formed by a pair of opposed rigid plastic members 92 and 94. Once again, each of the two opposed rigid plastic members 92 and 94 are constructed in the same manner as indicated in connection with the embodiment in FIG. 5 of the drawings, including the adhesive system as heretofore described. However, the upper rigid plastic member 92, as viewed in the drawings, further includes a nichrome heating wire loop 95 which is positioned centrally with respect to the central opening well 93. The nichrome heating wire loop 95 includes a pair of wire leads 96 and 97 which extend through the body portion of the plastic member 92 terminating externally of the periphery thereof in order to accommodate the interconnection with a voltage source as generally illustrated by the numeral 98 (FIG. 9). The construction of the rigid plastic member 92 further includes the provision of an adhering protective membrane 99 which overlies the film of adhesive 101. The contacting face of the protective membrane 99 is further provided with its own adhesive 103 thereby to carry a protective cover that is removed prior to adhesively joining connectors. It will therefore be appreciated that the two opposed rigid plastic members 92 and 94 may be adhered together by removing the protective covers 105 thereby to expose the adhesive 103 carried on the protective membrane 99. It will further be observed that the nichrome heating wire loop 95 is positioned immediately behind the membrane 99 carried by the rigid plastic member 92 such that the area immediately above the central opening well 93 is bowed outwardly a slight distance. Hence, when the two members 92 and 95 are adhesively joined together, a slight degree of pressure is exerted against the opposed protective membrane 99 overlying the corresponding central opening well 93 of the member 94.

In order to establish the common collection chamber 107, (FIG. 11) the wire leads 96 and 97 are connected to a voltage source 98 such that the nichrome heating wire loop 95 may be electrically energized. The heat carried by energizing the wire loop 95 will effectively sterilize, seal and penetrate the membranes 99 associated with each of the two rigid plastic members 92 and 94 to establish the common chamber 107 to permit fluid communication between the opposed channel conduits 102 and 104.

Figure 10:
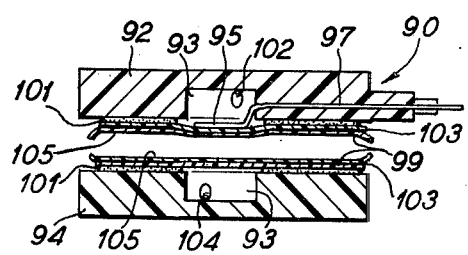
FIG. 10 is a side elevational view, in cross section, showing the details of construction of the sterile connector formed by two rigid plastic members and incorporating the resistance heating wire loop underlying one of the protective covers and film of adhesive and prior to joining the members together.
Figure 11:
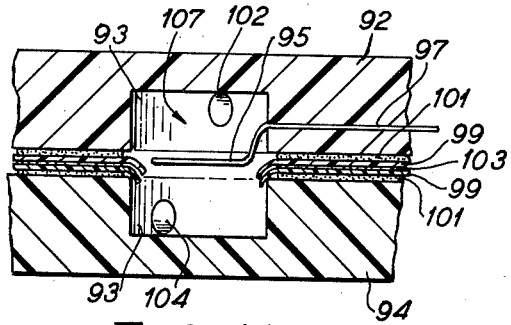
FIG. 11 is a side elevational view, in cross section, and partially broken away, showing the sterile connector as exemplified in FIG. 10 but with the membranes penetrated by the action of the resistance heating wire loop.

It will therefore be appreciated that the principal difference between the embodiments illustrated in FIGS. 9, 10 and 11 of the drawings and the prior described embodiments is simply the provision of the nichrome heating wire loop 95 with the associated protective membranes 99 in order to obtain sterility of the environment surrounding the common collection chamber 107, and to establish the chamber 107 initially.

Figure 12:
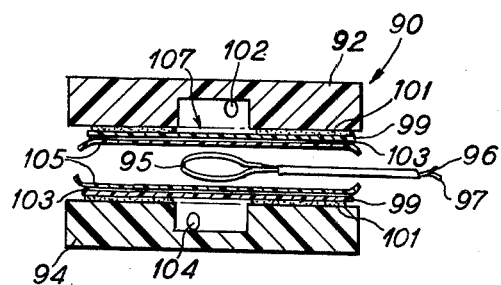
FIG. 12 is a side elevational view, in cross section, showing a sterile connector formed by two rigid planar plastic members and wherein the resistance heating wire loop is positioned between the members prior to joining the members together adhesively.
Figure 13:
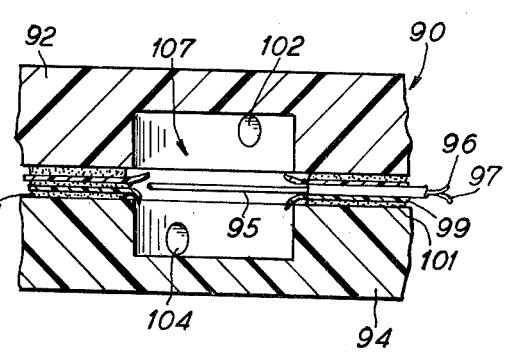
FIG. 13 is a side elevational view, in cross section, and partly broken away, showing the embodiment of the sterile connector as exemplified in FIG. 12, but with the common collection chamber being formed by the action of the nichrome heating wire loop.

With regard to FIGS. 12 and 13 of the drawings, a modified version of the embodiment as depicted in FIGS. 10 and 11 is illustrated. For the sake of convenience, like numerals are utilized to designate like parts as shown and described in connection with FIGS. 10 and 11. It will be observed that the only difference in this embodiment is that the nichrome heating wire loop 95 with the associated wire leads 96 and 97 are provided between the joining faces of the respective rigid plastic members 92 and 94 such that the nichrome heating wire loop 95 and associated leads 96 and 97 need not be molded into the body portion of rigid plastic member 92. It is contemplated that in use, the nichrome heating wire loop assembly 95 will be provided as a separate package and may be positioned by the operator between the contacting faces of the rigid members 92 and 94 during assembly. Once again, the wire leads 96 and 97 may be provided with coupling elements (not shown) to permit the coupling contact with a voltage source (similarly not shown). It will be apparent that in this embodiment, the nichrome heating wire loop 95 makes pressing contact with the protective membrane 99 on each of the two members 92 and 94. Hence, upon the application of sufficient heat, the wire loop 95 will penetrate the membranes 99 in order to establish the common collection chamber 107 as well as to sterilize the environment thereabout.

Figure 14:
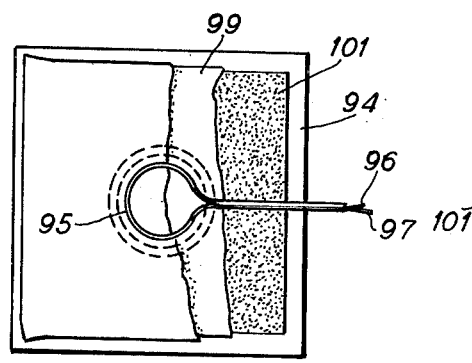
FIG. 14 is a top view, partly in cross section, showing the details of the sterile connector mount for insertion between two connectors as shown in FIGS. 12 and 13.

In FIG. 14, a top view of the assembly as described in connection with FIGS. 12 and 13 is illustrated, merely for the purpose of showing the relationship of one member to the next.

With reference to FIGS. 15 and 16 of the drawings, still another embodiment of the sterile connector is illustrated. The sterile connector 110 is formed by opposed rigid plastic members 112 and 114 respectively. As particularly shown in FIG. 16, each of the rigid plastic members 112 and 114 is shown to include a central opening well 115, and an offset bud well 118. It will be observed that the bud well 118 is in open communication with the central opening well 115 and in effect, forms an offset portion of the well 115. It will also be observed that each of the two plastic members 112 and 114 are identically designed and each is shown to further include an elongate groove 119. The adhesive system and membrane system is essentially the same as described in connection with the embodiments shown in FIGS. 10 through 14 of the drawings. The contacting faces of the rigid plastic members 112 and 114 each include a film of adhesive 121 which borders and is spaced slightly inwardly from the periphery of the central opening well 115 and the bud well 118. Overlying the film of adhesive 121 is a protective membrane 123 which includes an aperture 124 which is adapted to be positioned immediately above the corresponding bud well 118. The contacting surface of the protective membrane 123 is provided with an adhesive film 126 which is located in all areas excepting the immediate areas defining and overlying the central opening well 115 and the bud well 118. As indicated previously, the area of the protective membrane 123 overlying the bud well 118 is apertured as shown at 124 functions in a manner to be more fully described hereinafter. As further indicated previously, an alternative construction is to provide membranes which are heat sealed to the surface of the rigid bodies.

Each of the two rigid plastic members 112 and 114 is also provided with a pull tab cover 128 constructed in the same manner as described in connection with FIGS. 1 and 2 of the drawings. The short fold 129 of the pull tab 128 is adhered over the bud well 118 by adhesive encircling the well 118 and additionally crosses the groove 119 positioned in the face of the contacting surface of the corresponding member 112 and 114. The long fold 130 is folded back and over the short fold 129, and again overlies the groove 119 as well as the bud well area 118.

As illustrated in FIGS. 15 and 16 of the drawings, two like rigid plastic members 112 and 114 may be joined together to form the sterile connector 110. In order to form a common collection chamber, generally illustrated by the numeral 132, the operator need only grasp the long fold 130 of the pull tab covers 128 and remove the same from between the joined faces of members 112 and 114.

As indicated previously, the protective membranes 123 covering each of the two contacting faces of the rigid plastic members 112 and 114 fully overlie the entire area with the exception of the aperture 124 located therein which overlies the bud wells 118. Hence, when the pull tab covers 128 are removed, the common collection chamber 132 is formed so that fluid communication is achieved between the corresponding conduits 133 and 134 respectively.

In FIGS. 17, 18 and 19 of the drawings it will be observed that a rigid plastic member 112 of the type shown in FIGS. 15 and 16, may further be utilized in connection with still another type of connector described hereinbelow.

As shown in FIGS. 17 through 19, rigid plastic member 112 may be joined to a rigid plastic member 142 which is constructed to include a central opening well 145. The contacting face of member 112 also includes a tongue 146 mounted thereon and extending upwardly therefrom. The tongue 146 is designed and constructed to nestingly mate with the groove 119 located in the rigid plastic member 142 for a purpose to be more fully described hereinafter. It will further be observed that the rigid plastic member 142 is provided with a nichrome heating wire loop 148 which is positioned within the peripheral confines of the corresponding central opening well 145, and includes wire leads 149 and 150 extending laterally outwardly therefrom through the body of the rigid plastic member 142 adapted to be connected to a voltage source as indicated previously in connection with the embodiments as shown in FIGS. 10 through 14 of the drawings. The contacting face of rigid plastic member 142 is adhered to a protective membrane 152 thereon. The protective membrane 152 completely overlies the contacting face of the rigid plastic member 142 such that it overlies the area immediately above the central opening well 145. As shown in FIG. 17, the nichrome heating wire loop 148 presses against the protective membrane 152, which in turn, causes some degree of pressure against the opposed protective membrane 123 carried by the opposed rigid plastic member 112.

Once again, the protective membrane 152 carries an adhesive film 154 on the contacting face thereof such that the adhesive films 154 and 126 on the rigid plastic member 112 will function to join the two members together, excepting that the protective membrane carries no adhesive in the area to be penetrated by the heating wire loop.

It will be appreciated that when the two rigid plastic members 112 and 142 are joined together, the respective central opening wells 115 and 145 will be entirely covered by the corresponding protective membranes 123 and 152. In addition, it will be recalled that the rigid plastic member 112 is provided with a pull tab cover 128 which includes a long fold 130 extending outwardly therefrom. As shown in FIG. 17 of the drawings, when rigid plastic member 112 is joined to plastic member 142, the tongue 146 will be nested within the elongate groove 119. It will therefore be appreciated that the tongue 146 will capture the short fold 129 and the long fold 130 of the pull tab cover 128 within the elongate groove 119 such that unauthorized removal of the pull tab cover 128 over the bud well 118 cannot occur. Hence, since the pull tab cover 128 covers the aperture 124 located in the protective membrane 123, any and all communication between the two rigid plastic members 112 and 142 via the preformed opening in the plastic membrane over the bud well is prevented. The only manner in which a common collection chamber 156 can be established is by energizing the nichrome heating wire loop 148 in order to generate sufficient heat to sterilize, seal and penetrate the two membranes 123 and 152 respectively. In this posture, the common collection chamber 156 is formed, while at the same time assuring sterility by excluding the contaminants of the outer environment external to the sterile connector per se.

In addition, it now becomes apparent that the rigid plastic member 112 constructed as described, including a bud well 118 may be employed either with a like type of rigid plastic member 112, or may be employed in connection with a rigid plastic member 142 which employs a nichrome heating wire loop 145 system. Furthermore, it will now be appreciated that the provision of the bud well 118 along with the system of providing a pull tab cover 128 as well as a tongue 146 and groove 119 arrangement insures that the rigid plastic member 112 may be used in conjunction with either of the two types of opposing members to form a sterile connector and to insure the sterility and environmental integrity of the common collection chamber formed therebetween.

One of the important features in terms of providing sterile connectors of the type described herein is to have a pull tab system which cooperates with the adhesive surface of the members forming the sterile connector in order to achieve a differential bonding arrangement. As was indicated previously, the pull tab covers are removed by manually pulling on the long folds of the corresponding pull tabs such that the short folds thereof will progressively expose the corresponding central opening wells to one another in order to form a common collection chamber. This action occurs once the two contacting faces of the members forming the sterile connector are adhesively applied together. It is therefore apparent that the bond created between the pull tab and the adhesive film must be sufficient in order to initially seal the underlying preformed opening over the central opening or bud well; must have proper release characteristics so that the pull tabs may be progressively removed without disturbing the underlying adhesive film, while still preserving the sterility and integrity of the resulting common collection chamber. It has been found that there are three basic characteristics which must be complied with in order to achieve the desired result: (1) there must be sufficient adhesive to give a proper seal and exclude the environment including the contaminants; (2) the tab cooperating with the adhesive must establish a proper rolling release movement in order to prevent sliding contamination which would occur if the adhesive were to adhere to the pull tab during removal; and (3) once the tabs are removed, the adhesive must be sufficiently tacky so that the two adhesive surfaces properly adhere to one another and establish a proper seal therebetween in order to maintain sterility and exclude contaminants. It has been found that if the pull tab covers are made of a Mylar film and if the pull tabs or the adhesive surfaces is treated with a release agent, a more efficient differential bonding relationship will result. For example, it has been found that by treating the Mylar pull tab cover with a silicone release agent, and in addition, a wax is provided to wax the silicone release agent into the Mylar pull tab cover, the above differential bonding characteristics will be achieved. Alternatively, one may treat the adhesive to achieve the same differential bonding effect. It has been found that if the silicone release agent is used alone to treat either the adhesive area of the Mylar pull tab cover, the silicone release agent has a tendency to adulterate the adhesive and this will destroy the adhesive bonding characteristics between the adhesive and the Mylar pull tab cover. However, it has been found that where a wax is applied over the area treated with the silicone release agent, the wax agent has a tendency to prevent the adulteration of the adhesive by the silicone agent and thereby facilitates the removal of the pull tab cover while still preserving the adhesive tackiness necessary in order to form a good bond between the joining faces of the members of the sterile connector.

It has also been found that there is a critical relationship between the thickness of the pull tabs and the thickness of the adhesive layer insofar as the molded sterile connector members are concerned. Reference is had to the sterile connectors are exemplified in FIGS. 5 and 7 through 19 of the drawings. It will be appreciated that since both of the adhesive layer and the pull tabs have a thickness dimension, if the thickness is not properly adjusted, there is a tendency to interfere with the bridging action which must occur once the pull tab covers have been removed and this has a direct impact upon a proper seal being achieved between the contacting faces of the members of the sterile connector. Hence, it has been found that if one increases the thickness of the adhesive layer and keeps the thickness of the pull tab to a certain minimum level, the removal of the pull tabs effect the desired seal between the corresponding adhesive films. In this connection, ideal operating parameters have been found if the adhesive thickness is between 5 and 15 mil, and pull tab thickness is between $\frac{1}{4}$ to $\frac{1}{2}$ mil in thickness, there is a ratio of 20 to 1 because of the combined thickness of the adhesive film is between 10 and 30 mil, and the combined thickness of the pull tabs is between $\frac{1}{2}$ and 2 mil, and hence there is a bridging action occurring and hence, upon removal of the pull tabs, the adhesive is able to effect a proper seal between the two members of the sterile connector.

As was indicated previously, where the members forming the sterile connector are intended to be molded from a plastic resin material, the members may be color coded to indicate multiple connecting channels as well as to distinguish outer members from intermediate members as was illustrated in FIG. 8 of the drawings. In addition, the color coding can be keyed into the types of solutions which are to be channeled through the respective member, for example, a red color signifying interconnection with a container or source of supply of whole blood.

In addition, it is contemplated that the members of the sterile connector may be provided with alignment pins in order to facilitate the proper alignment of the corresponding members when joined together to form the sterile connector. While this feature is not shown in the drawings, nevertheless, alignment pins in connection with devices of this type is within the skill of the art.

In connection with the embodiments of the invention utilizing the nichrome heating wire loop, it is further contemplated to be advisable to employ an insulation about the wire so that upon charging the nichrome heating wire loop, one eliminates the possibility of oxidation on the surface of the wire which might contaminate fluids passing through the common collection chamber. In this connection, it has been found ideal to employ a polyimide film sold under the trade name Kapton. It has been found that this material when employed as an insulation around the nichrome heating wire loop prevents direct contact between the fluids and the metallic portion of the wire loop and hence excludes and prevents any material transfer from the wire loop, such as oxidation products, to the fluids passing therethrough.

It will be appreciated from the above description that when the invention defined herein is viewed in its various parameters, there has been provided a system for constructing sterile connectors which will meet most of the requirements currently found in the industry. In addition, the sterile connectors provided by this invention are basically simplified in construction, while nevertheless providing a more secure sterile environment in connection with the common collection chamber formed therein. The pull tab system provided further simplifies the degree of manipulation necessary in order to construct the sterile connector on situs by the operator. In addition, the pull tab system has been improved by improving the differential bonding characteristics between the adhesive and pull tab system by treating one or the other with a silicone release agent, and then employing a wax in order to wax in the silicone release agent and prevent the silicone release agent from adulterating the adhesive. In this manner, the seal obtained between the adhesive films is insured in order to preserve the integrity of the surrounding environment.

It is submitted that by virtue of the present invention. an improved but simplified sterile connector system has been provided. It will further be noted that the system as set forth herein presents a variety of embodiments which basically employ the same overall conceptual system, but can manifest itself in a variety of embodiments to apply to various usages.

While there is described what is at present to be considered to be the preferred embodiments of the invention, it will be understood that various modifications may be made therein, and it is intended to cover in the appended claims all such modifications as fall within the true spirit and scope thereof.

What is claimed is:

1. A sterile connector for connecting separated fluid sources characterized in that each of the separated fluid sources includes a conduit in fluid communication with the fluid, comprising in combination, at least two polygonal planar plastic members having substantially the same configuration, said members being joined face-to-face in matching relationship in order to present a substantially common periphery of said joined members, a common collection chamber positioned substantially centrally between said joined members and said collection chamber being substantially formed by said joined planar plastic members a film of adhesive positioned on the joining faces of said planar plastic members for holding the contacting faces thereof together, a pair of pull tab covers overlying said film of adhesive on a corresponding joining face of each of said plastic members and overlying said common collection chamber, and further including a portion of said pull tab covers extending laterally outwardly beyond the periphery of said polygonal planar plastic members, said joined planar plastic members being adapted to contain at least two spaced fluid flow paths extending from outside the joined plastic members and through said adhered members to communicate with the common collection chamber, whereby said planar plastic members may be adhesively joined in surrounding relation about said spaced fluid flow paths to establish a fluid path between the separated fluid sources under sterile conditions through said common collection chamber, when said pull tab covers are removed from overlying relation with said common collection chamber.

2. The sterile connector as set forth in claim 1 wherein each of said polygonal plastic members is formed by an outer, thin, flexible plastic unit of sheetlike construction having an exterior surface and a contacting surface, an intermediate, thin, flexible plastic sheet-like unit having a configuration corresponding to said outer unit, said intermediate unit having a reverse side disposed towards said contacting surface of said outer unit and an adherent side.

said intermediate unit including a substantially central opening positioned therein, the central opening of each of said intermediate units being in registry with one another thereby to form said common collection chamber when joined together, sealing means interposed between said contacting surface of said outer unit and said reverse side of said intermediate unit to sealingly mate said units and form a corresponding polygonal planar plastic member, said sealing means being absent only in the area immediately surrounding said central opening, each of said polygonal planar plastic members including a fluid flow path interposed between said outer unit and said intermediate unit and extending between the outer periphery of said polygonal plastic member and said common collection chamber thereby to permit fluid communication therethrough, a film of adhesive positioned on the adherent side of said intermediate unit for joining opposed ones of said intermediate units together, said adhesive being absent from the area immediately surrounding said central opening, a pair of pull tab covers, one of each of said pull tab covers positioned over a corresponding central opening, each pull tab cover being a thin elongated strip of foldable material and including a short fold overlying a portion of said film of adhesive and further overlying said central opening and being folded flat against a long fold of said pull tab cover such that each of said long folds overlies said corresponding short fold and extends laterally outwardly beyond the periphery of said polygonal planar plastic member, said pull tab cover and film of adhesive characterized by differential adhesive bonding so that a pulling force exerted on said long fold externally of said sterile connector progressively exposes said central openings to form said common collection chamber as said polygonal planar plastic members are joined together by contacting the respective adherent sides of said corresponding intermediate units.

3. A sterile connector as set forth in claim 2, wherein said fluid flow path is defined by a substantially linear pathway devoid of said sealing means whereby said outer unit and said corresponding intermediate unit are unadhered along the length of said flow path such that fluid communication may be established between said common collection chamber and the outer periphery of such sterile connector.

4. A sterile connector as set forth in claim 3, wherein said fluid flow path associated with each one of said polygonal planar plastic members comprises a conduit arrested between said outer unit and said intermediate unit, and having an inner end terminating in said common collection chamber and an outer end terminating externally of the periphery of said sterile connector body, such that said sterile connector body, when assembled, includes a pair of conduits, each one in fluid communication with said common collection chamber and extending externally outwardly from said sterile connector body.

5. The sterile connector as set forth in claim 4, wherein the inner end of one of said conduits is characterized by the provision of a male coupling element, and the other of said conduits is characterized by the provision of a female coupling element, such that the inner ends of said conduit may be coupled in said common collection chamber, said coupling permitted by the coupling action associated with said male and female coupling elements.

6. A sterile connector as set forth in claim 3, wherein each of said polygonal planar plastic members has a quadrilateral configuration.

7. A sterile connector as set forth in claim 6, wherein each of said conduits enters said connector body from opposite corners of the said quadrilateral members, and said pair of pull tab covers are positioned along one of the opposed pair of opposite corners.

8. A sterile connector as set forth in claim 1, wherein said polygonal planar plastic members are each formed as rigid plastic members, having a thickness substantially less than the length of a side thereof, and wherein said common collection chamber is formed, at least in part, by a substantially central opening formed in the contacting side of each of said rigid plastic members, said central openings being in registry when said film of adhesive operates to join said rigid plastic members together, and said conduits extend from outside said connector body through said body of each of said rigid plastic members and having the inner ends thereof in fluid communication with each of said central openings and positioned below the contacting side of the corresponding rigid plastic member.

9. A sterile connector as set forth in claim 8, wherein each of said central openings in said rigid plastic members comprises a well centrally positioned relative to said rigid plastic member, and extending inwardly from the contacting side of said rigid plastic member, and said conduit is formed by a defined channel extending through the body portion of said rigid plastic member having the inner end opening within the confines of said well, and the outer end terminating in a sidewall of said rigid plastic member.

10. A sterile connector as set forth in claim 9, wherein each of said rigid plastic members further includes a pull tab cover consisting of a thin, elongated strip of foldable material, and including a short fold overlying a portion of said film adhesive and further overlying said well, and being folded flat against a long fold of said pull tab cover such that each of said long folds overlies said corresponding short fold and extends laterally outwardly beyond the periphery of said rigid plastic member, said pull tab cover and film of adhesive characterized by differential adhesive bonding so that a pulling force exerted on said long fold externally of said sterile connector progressively exposes said well to form said common collection chamber as said polygonal planar rigid plastic members are joined by contacting the respective contacting sides of said corresponding rigid plastic members.

11. A sterile connector as set forth in claim 10, wherein each of said rigid plastic members has a quadrilateral configuration.

12. A sterile connector as set forth in claim 10, wherein said channels forming said conduit each traverse said body between said well and a sidewall, said channels formed and said joined members extending in diametrically opposed directions from said common collection chamber, and said pull tab covers are each positioned along a radial path spaced from each of said conduit channels.

13. A sterile connector for connecting separated fluid sources characterized in that each of the separated fluid sources includes a conduit in fluid communication with the fluid, comprising in combination, at least two polyhedral planar plastic members having substantially the same configuration and each defined by an outer periphery having opposed surfaces, said polyhedral planar plastic members being formed as rigid members having a thickness substantially less than the length of a side thereof, one of said plastic members having a traversing central opening positioned therein and traversing said member from one surface to the opposed surface, each of said remaining plastic members including a central opening formed as a well therein and positioned to be in registry with said traversing central opening when said plastic members are joined together in stacked relation such that said central opening and said traversing central opening together form a common collection chamber, each of said plastic members including at least one fluid flow path formed therein and positioned to establish fluid communication between said corresponding central opening and said outer periphery of said corresponding plastic member, each of said plastic members including a film of adhesive positioned on at least one of the opposed surfaces thereof to permit at least two of said plastic members to be joined together in face to face relation with said central openings in registry, at least a pair of pull tab covers, one of each of said pull tab covers positioned over a corresponding opening, each pull tab cover being a thin elongated strip of foldable material and including a short fold overlying a portion of said film of adhesive and further overlying said central opening and being folded flat against a long fold of said pull tab cover such that each of said long folds overlies said corresponding short fold and extends laterally outwardly beyond the periphery of said corresponding plastic member, said pull tab cover and film of adhesive characterized by differential adhesive bonding so that a pulling force exerted on said long externally of said sterile connector progressively exposes said central openings to form said common collection chamber as said polyhedral planar plastic members are joined together by contacting the respective adhesive surfaces to form a sterile connector body, whereby when said planar plastic members are joined together, said central opening and traversing central opening function to define said common collection chamber, with said fluid flow paths establishing fluid communication between said separated fluid sources when the conduits thereof are interconnected with said fluid flow paths, through said common collection chamber.

14. A sterile connector as set forth in claim 13 wherein said film of adhesive is provided on both of the opposed surfaces of said planar plastic member having said traversing central opening, and said pull tab covers similarly positioned on each of the opposed surfaces of said plastic member, whereby said planar plastic member having said traversing central opening is adapted to accommodate another rigid planar plastic member adhesively joined on each of the opposed surfaces thereof.

15. A sterile connector as set forth in claim 14, which further includes at least three planar plastic members, said plastic member having said traversing central opening being positioned intermediate said remaining plastic members, said central openings in said remaining planar plastic members cooperating with said traversing central opening in said intermediate plastic member thereby to form a common collection chamber, and said fluid flow paths located in each of said plastic members permitting fluid communication between said common collection chamber formed by said joined plastic members and the outer periphery thereof in order to permit fluid communication between at least three separated fluid sources.

16. A sterile connector as set forth in claim 15, which further includes a plurality of planar plastic members joined in stacked relationship, and including a plurality of intermediate plastic members, each of said intermediate plastic members formed with a traversing central opening and having a film of adhesive positioned on each of the opposed surfaces thereof, said intermediate plastic members being interposed between a final plastic member at one end of said stacked members and an opposed final plastic members being formed with a central opening or as a well therein and having an inherent surface having the film of adhesive positioned thereon, in an external surface, whereby a plurality of said intermediate plastic members may be joined together and bounded by a pair of opposed final plastic members to provide a manifold sterile connector establishing fluid communication through the respective fluid paths positioned therein with said common collection chamber formed by said manifold sterile connector in order to permit fluid communication between a plurality of separated fluid sources.

17. A sterile connector as set forth in claim 9, which further includes a thin, flexible protective plastic cover overlying said film of adhesive thereby to protect the sterility of said rigid plastic member until a pair of said plastic members are joined together.

18. A sterile connector as set forth in claim 17, which further includes a nichrome heating wire loop positioned against at least one of said protective plastic covers overlying said film of adhesive, conductor means extending laterally outwardly from said nichrome heating wire loop to a point externally of said rigid plastic member, said conductor means adapted for connection to a voltage source, whereby upon energizing said nichrome heating wire loop, sufficient heat is generated to destroy said plastic protective cover to establish said common collection chamber.

19. A sterile connector as set forth in claim 18, wherein said nichrome heating wire loop is positioned in a well of one of said rigid plastic members, and said conductor means comprises a pair of conductor leads extending laterally through the body portion of said corresponding rigid plastic member to the external periphery thereof and adapted for interconnection to a voltage source.

20. A sterile connector as set forth in claim 18, wherein said nichrome heating wire loop is positioned between adjoining adhered rigid plastic members, and said conductor means comprises a pair of conductor leads extending laterally between said protective plastic covers to a point external of the periphery of said sterile connector and adapted for connection to a voltage source.

21. A sterile connector as set forth in claim 18, wherein said nichrome heating wire loop is encased with an insulation material thereby to insulate said wire loop and prevent wire contact with the fluid traversing through said common collection chamber during use.

22. A sterile connector as set forth in claim 18, wherein at least one of said rigid plastic members having said well formed therein further includes a bud well adjoining and in open communication with said well formed therein and positioned in offset relationship thereto, said rigid body having said bud well formed therein and further having a straight groove extending across the contacting face thereof and reaching to adjoining sides thereof, the opposed one of said rigid plastic members having a straight tongue positioned to seat within said groove of said opposed rigid plastic member when the contacting faces are joined together, said nichrome heating wire loop fixed to said rigid body having said tongue positioned thereon, said pair of pull tab covers adapted to be seated and locked by said tongue in groove arrangement between said pair of rigid plastic members when said common collection chamber is established by energizing said nichrome heating wire loop, and being in a free pull posture with two of said rigid plastic members each having the groove adjoined together to permit the pull tab covers to be moved to establish the common collection chamber therein and similarly expose said bud well in conjunction with said common collection chamber.

23. A sterile connector as set forth in claim 22, wherein said rigid plastic members are quadrilateral, and said interconnecting tongue and grooves in opposed ones of said rigid plastic members extend to connecting sides of said quadrilateral member at a corner thereof.

24. A sterile connector as set forth in claim 22, wherein said pull tab cover on each of said rigid plastic members remains in overlying relation with regard to said bud well when said common collection chamber is established by energizing said nichrome heating wire loop such that said bud well remains covered with respect to the adjoining faces of said opposed rigid plastic members.

25. A sterile connector as set forth in claim 22, wherein said rigid plastic member having said nichrome heating wire positioned therein further includes said conduction means extending laterally outwardly through said body portion of said rigid plastic member from said nichrome heating wire loop to a point external to the periphery of said rigid plastic member and adapted for interconnection with an energizing source.

26. A sterile connector as set forth in claim 25, wherein said conduction means comprises a pair of conduction leads traversing said body portion terminating at the outer periphery of said rigid plastic members with corresponding male and female sockets thereby to be adapted for interconnection by coupling action to an energizing source having correspondingly mating male and female sockets.

* * * * *